United States Patent
Bromley et al.

(10) Patent No.: US 9,237,922 B2
(45) Date of Patent: Jan. 19, 2016

(54) HAND-HELD ELECTROSURGICAL INSTRUMENT

(76) Inventors: Robert L. Bromley, El Paso, TX (US); Richard P. Fleenor, Englewood, CO (US)

(*) Notice: Subject to any disclaimer, the term of this patent is extended or adjusted under 35 U.S.C. 154(b) by 931 days.

(21) Appl. No.: 13/405,923

(22) Filed: Feb. 27, 2012

(65) Prior Publication Data

US 2012/0221000 A1 Aug. 30, 2012

Related U.S. Application Data

(60) Provisional application No. 61/447,562, filed on Feb. 28, 2011.

(51) Int. Cl.
| | |
|---|---|
| A61B 18/14 | (2006.01) |
| A61B 19/00 | (2006.01) |
| A61B 18/00 | (2006.01) |
| A61B 17/00 | (2006.01) |

(52) U.S. Cl.
CPC ......... *A61B 18/1402* (2013.01); *A61B 19/5202* (2013.01); *A61B 2017/00734* (2013.01); *A61B 2018/00916* (2013.01); *A61B 2019/521* (2013.01)

(58) Field of Classification Search
CPC .............. A61B 19/5202; A61B 2018/00916; A61B 2019/4836; A61B 2019/507; A61B 2019/521
See application file for complete search history.

(56) References Cited

U.S. PATENT DOCUMENTS

| | | |
|---|---|---|
| 4,562,838 A | 1/1986 | Walker |
| 4,688,569 A | 8/1987 | Rabinowitz |
| 5,061,268 A | 10/1991 | Fleenor |
| 5,098,430 A | 3/1992 | Fleenor |
| 5,246,440 A | 9/1993 | Van Noord |
| 5,306,238 A | 4/1994 | Fleenor |
| 5,484,435 A | 1/1996 | Fleenor et al. |
| 5,843,080 A | 12/1998 | Fleenor et al. |
| 6,053,910 A | 4/2000 | Fleenor |
| 6,083,221 A | 7/2000 | Fleenor et al. |
| 6,214,000 B1 | 4/2001 | Fleenor et al. |
| 6,454,764 B1 | 9/2002 | Fleenor et al. |
| 6,562,032 B1 | 5/2003 | Ellman et al. |
| 6,648,902 B2 | 11/2003 | Colgan et al. |
| 6,666,859 B1 | 12/2003 | Fleenor et al. |
| 7,166,102 B2 | 1/2007 | Fleenor et al. |
| 7,367,971 B2 | 5/2008 | Fleenor et al. |
| 2007/0049927 A1 | 3/2007 | Saltzman |
| 2009/0076504 A1 | 3/2009 | Schnitzler |
| 2010/0145333 A1 | 6/2010 | Dethier et al. |

FOREIGN PATENT DOCUMENTS

WO 2004/054626 A2 7/2004

*Primary Examiner* — Deborah Malamud
(74) *Attorney, Agent, or Firm* — Marsh Fischmann & Breyfogle LLP

(57) ABSTRACT

Electrosurgical instruments and associated methods are provided. An electrosurgical instrument may include one or more light emitters that comprise a light source in operative communication with a power supply supportably interconnected to a handle portion. The instrument may have a toggle member with one or more selectable positions that may selectively activate any of one or more operational states of an electrosurgical electrode comprising the instrument. The toggle member may selectively activate the light emitter(s) provided on the instrument alone and/or in conjunction with the activation of one or more operational state. The handle portion may include an elastomeric handle portion that extends continuously along the handle portion and over the toggle member to seal the handle portion.

36 Claims, 13 Drawing Sheets

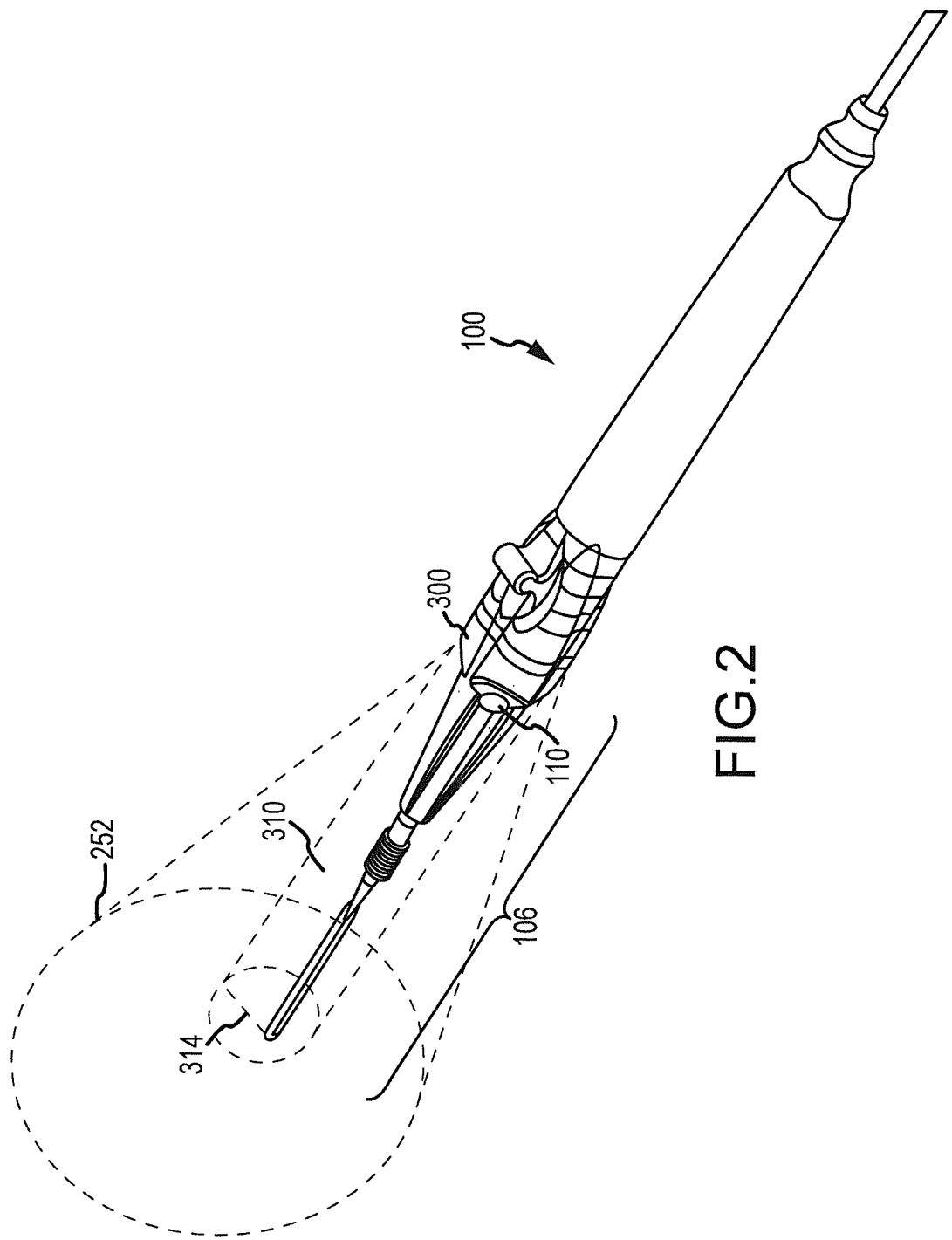

HAND-HELD ELECTROSURGICAL INSTRUMENT

RELATED APPLICATION

This application claims priority to U.S. Provisional Patent Application No. 61/447,562, filed Feb. 28, 2011, entitled "HAND-HELD ELECTROSURGICAL INSTRUMENT," which application is incorporated herein by reference in its entirety.

FIELD OF THE INVENTION

The present invention generally relates to surgical instruments, and more particularly to hand-held electrosurgical instruments.

BACKGROUND OF THE INVENTION

Electrosurgery is a well-known surgical approach employed to reduce tissue damage and blood loss during operating room and outpatient procedures. In electrosurgery, tissue of a patient adjacent to an electrode conductor is excited by a high frequency electric current passing from the electrode conductor to the tissue of the patient. Depending upon the characteristics of the electrical current and method employed by a user, different electrosurgical operations may be performed with the electrosurgical instrument. For instance, an electrosurgical instrument may be used to cut, coagulate (coag), desiccate, or fulgurate tissue.

As with many surgical instruments, electrosurgical instruments may require the user to accurately and precisely guide the electrosurgical instrument when performing an electrosurgical operation. In this regard, consistent pressure and stability are necessary to realize accuracy when using the electrosurgical instrument. As such, an electrosurgical instrument may be of a size such that the electrosurgical instrument may be readily gripped by the user to accurately and precisely maneuver the electrosurgical instrument. For example, many electrosurgical instruments are similar in size and shape to a writing instrument.

The high frequency electrical current used to perform various electrosurgical operations may be generated by electrosurgical equipment (e.g., an electrosurgical generator). In turn, a signal cable may extend between the electrosurgical instrument and the electrosurgical equipment to facilitate electrical communication therebetween.

In this regard, when electrosurgical instruments rest on a surface (e.g., an operating room table, the patient, etc.) the instruments may be free to roll about a longitudinal axis of the electrosurgical instrument, which may result in inadvertent activation of the electrosurgical instrument. This increases the potential for injury to the user and/or patient and may result in damage to the electrosurgical instrument.

The signal cable extending from the electrosurgical instrument to the electrosurgical equipment may have a certain amount of elastic memory. This may cause the electrosurgical instrument to roll when disposed on a support surface such that a side load on one or more of the actuators may activate the electrosurgical instrument. Furthermore, if an electrosurgical instrument is to roll off a support surface and fall, the electrosurgical instrument may be damaged as a result of the fall.

Electrosurgical instruments may also have independent actuators to activate one or more operational states. These independent actuators may require a user to reposition one or more fingers with respect to the electrosurgical instrument to control the different actuators. This may result in inconsistent pressure, create movement, and reduce the stability of the electrosurgical instrument, thus leading to reduced accuracy.

Additional devices maybe employed during an electrosurgical operation. For instance, operating room lighting may allow a user to have an improved view of the surgical field. In this regard, lighting arrays may be provided in operating rooms or outpatient clinics to assist in illuminating the surgical field. Additionally or alternatively, bulky fiber-optic cable can also be used to illuminate the surgical field by being placed in or near the surgical field. Additional light emitters, such as headlamps and the like, worn by medical personnel may also be employed. However, in all these instances the light emitter is generally provided some distance away from the electrosurgical instrument, and/or away from the surgical field. As such, the surgical instrument and light emitters are separated and shadows may be cast on the surgical field by the user, the electrosurgical instrument, or other obstructions (e.g., table drapes, other devices utilized during surgery, user's hand, etc.). In short, known light emitters may fail to provide a sufficient amount of unobstructed light at the surgical field of interest.

SUMMARY OF THE INVENTION

In view of the foregoing, a primary objective of the present invention is to provide an improved electrosurgical instrument operation and environment.

Another objective is to provide an improved electrosurgical instrument and method that may be employed to enhance medical personnel efficiencies attendant to an electrosurgical procedure.

An additional objective is to provide an improved electrosurgical instrument that is relatively simple in construction and assembly.

Another objective is to provide an improved electrosurgical instrument that is less likely to inadvertently roll and inadvertently activate when disposed on a surface.

Yet another objective is to provide an improved electrosurgical instrument that facilitates an improved environment via enhanced illumination of the surgical field of interest, e.g., by eliminating the obstruction of light cast on the surgical field of interest.

Another objective is to provide an improved electrosurgical instrument that improves the ability of a user to accurately and precisely manipulate the surgical instrument when activating an operational state of the electrosurgical instrument.

Numerous additional features and advantages of the present invention will become apparent to those skilled in the art upon consideration of the embodiment descriptions provided hereinbelow.

In one aspect, a hand-held electrosurgical instrument is provided that includes a handle portion, and an electrosurgical electrode and light emitter supportably interconnected to the handle portion. The instrument further includes a toggle member that is supportably interconnected to the handle portion. The toggle member is manipulatable to effect activation of at least one operational state of the electrosurgical instrument, (e.g., to cut, coagulate, desiccate and/or fulgurate tissue utilizing a plurality of different electrosurgical signals supplied by electrosurgical equipment) and to effect emission of light from the light emitter.

The light emitter may include at least one light source supportably interconnected to the handle portion. Additionally, a power source may be supportably interconnected to the handle portion and operatively interconnected to the light source(s). In turn, the light source(s) may be selectively activatable by manipulation of the toggle member to emit light, free from interconnection to external energy sources.

In the latter regard, the electrosurgical instrument may be free from additional wire, power cables or remote light transmitters (e.g., fiber-optic cable) running between electrosurgical equipment and the electrosurgical instrument. Accordingly, drag applied to the hand of the user due to additional wire or cable resting on the user may be reduced. The elimination of additional wire or cable may also help to prevent wrist fatigue and grip fatigue, thus improving the endurance of the user using the electrosurgical instrument.

The toggle member may be selectively manipulated to at least a first position to effect activation of a first operational state of the electrosurgical instrument and to a second position to effect activation of a second operational state of the electrosurgical instrument. Additionally, the toggle member may be biased to a home position and selectively manipulatable from the home position to the first position and to the second position by a user. When the toggle member is in the home position, the electrosurgical instrument may be in an inactive state (e.g., such that the electrosurgical electrode and light emitter are both inactive).

Further, the toggle member may be provided to be selectively manipulated to a third position to effect simultaneous activation of both the first operational state of the electrosurgical instrument and the emission of light from the light emitter. Additionally, the toggle member may be provided to be selectively positionable to a fourth position to effect simultaneous activation of both the second operational state of the electrosurgical instrument and the emission of light from the light emitter. In some arrangements, the toggle member may be manipulated to a fifth position to independently activate the light emitter, without activating the electrosurgical instrument, e.g., by vertically depressing the toggle.

The toggle member may be directly manipulatable between the home position and any of the first position, the second position, the third position, the fourth position, or the fifth position. In this regard, the toggle member may comprise a single tactile interface point which allows the user to selectively activate any operational state of the electrosurgical instrument.

As may be appreciated, various implementations may be provided in which the toggle member may be randomly manipulated to activate the light emitter prior to activation of any operational state. Additionally or alternatively, various implementations may be provided in which the toggle member may be randomly manipulated to activate any operational state prior to activation of the light emitter.

In various embodiments, the toggle member may be selectively positionable in a first position to effect activation of a first operational state of the electrosurgical instrument, and in a second position to effect only the emission of light. In this regard, at least a portion of the toggle member may be manipulatable in a first dimension relative to the handle portion to effect activation of at least one operational state of the electrosurgical instrument, wherein the toggle member may be manipulatable in a second dimension to effect the emission of light.

In some arrangements, the electrosurgical electrode may be provided to extend away from a first end of the handle portion. At least a portion of the toggle member may be at least one of advanceable towards and retractable from the first end of the handle portion to effect activation of at least one operational state. In addition, at least a portion of the toggle member may be depressible relative to the handle portion to effect the emission of light.

In another aspect, a hand-held electrosurgical instrument is provided that includes an electrosurgical electrode and an elongate handle portion. The electrosurgical electrode is supportably interconnected to and extends away from a first end of the handle portion. At least a contoured segment of the handle portion may be configured to restrict rolling of the electrosurgical instrument when disposed on a support surface. Accordingly, the electrosurgical instrument may reduce the potential for inadvertent activation of the electrosurgical instrument and reduce the potential of the electrosurgical instrument falling from the surface.

In some embodiments, the electrosurgical instrument may include a signal cable fixedly interconnected to and extending away from a second end of the handle portion (e.g., opposite to the first end of the handle portion). The signal cable may be operatively interconnected to the electrosurgical electrode to provide a signal thereto from electrosurgical equipment.

The electrosurgical instrument may also include a toggle member supportably interconnected to the handle portion that is selectively manipulatable by a user to effect activation of at least one operational state of the electrosurgical instrument. The toggle member may be located on a first side of the contoured segment of the handle portion. The contoured segment may further include at least two additional sides located directly adjacent to the first side and to each other. Accordingly, in one embodiment, the two additional sides and the first side may define a triangular configuration along the contoured segment of the handle portion.

In some arrangements, the electrosurgical instrument may include at least three light sources that are disposed about an adjoinment region between the electrosurgical electrode and the first end of the handle portion to which the electrosurgical electrode is supportably interconnected. A longitudinal axis of the handle portion and a center axis of the electrosurgical electrode may be one of aligned or parallel such that the light sources are spaced about the center axis. In turn, enhanced illumination about the electrosurgical electrode eliminates electrode shadows.

Additionally, the electrosurgical instrument may include a triangularly-configured, light transmissive nose that is interconnected to the first end of the housing and disposed about the at least three light sources. The nose may taper away from the one end of the handle portion towards the center axis of the electrosurgical electrode. The contoured segment of the handle portion and the nose may be externally configured to define a conformal transition therebetween.

In another aspect, a hand-held electrosurgical instrument may be provided that is sealed from external fluids. For instance, an elastomeric material may be provided that covers and substantially encases at least a handle portion of the electrosurgical instrument. The elastomeric material may extend continuously and uninterrupted, and may be impenetrable to fluids. The elastomeric handle portion may seal one or more internal portions of the electrosurgical instrument.

In some embodiments, a proximal seal and a distal seal may be provided at either end of the continuously-extending, elastomeric handle portion to further isolate the interior of the electrosurgical instrument from fluids (e.g., fluids that come into contact with the instrument during an electrosurgical procedure such as bodily fluids, saline, etc.). The elastomeric handle portion may also provide a gripping surface designed to facilitate a non-slip interface between a user's hand (or a glove provided thereon) and the instrument.

Furthermore, in some embodiments, the elastomeric handle portion may extend continuously with respect to a toggle member. As such, the elastomeric handle portion may be deflectable at the toggle member to allow for selective manipulation of the toggle member. The elastomeric handle portion may remain continuous over the toggle member when deflected such that the toggle member is sealed regardless of the position of the toggle member.

In an additional aspect, a hand-held electrosurgical instrument may be provided that includes a handle portion, an electrosurgical electrode that is supportably interconnected to and extends away from a first end of the handle portion in a first direction, and a light emitter for emitting light in the first direction to illuminate a predetermined volume extending from the first end of the handle portion to a distal end of the electrosurgical electrode. The volume extends about a majority of the electrosurgical electrode.

The light emitter may be adapted to emit light from a plurality of locations spaced about an adjoinment region between the electrosurgical electrode and the handle portion. In some embodiments, the light emitter may include a plurality of light sources. Different ones of the plurality of light sources may be located at different ones of the plurality of locations for emitting light. For instance, the plurality of light sources may include at least three light sources disposed about an adjoinment region between the electrosurgical electrode and the handle portion. The light emitter may further include a light transmissive nose that is disposed about the at least three light sources.

The instrument may also include a power source that is supportably interconnected to the handle portion and operatively interconnected in series or parallel to each of the plurality of light sources. Accordingly, the plurality of light sources may be operable to emit light free from interconnection to external energy sources. The power source may include at least one power storage device, e.g., at least one battery. In one arrangement, the power source may include a plurality of batteries electrically interconnected in series or in parallel.

In one aspect, the light emitters may be a light emitting diode that emits at least 1,000 millicandela (mcd) of light. In turn, the light emitter may be activatable to illuminate the entirety of the predetermined volume with at least 1,000 mcd of light. In one embodiment, different ones of the plurality of light sources may emit light at corresponding different predetermined wavelengths. Additionally, the plurality of light sources may emit light of a color temperature of at least about 3,000K.

In relation to various embodiments described herein, the term "toggle member" is used only to describe the ability to activate different operational states and/or the emission of light. In turn, no particular structure or limited number of states is implied by use of the term "toggle", unless otherwise specified. For instance, a "toggle member" may be operative to selectively activate more than two operational states. As such, the term "toggle" is not intended to limit the functionality of the "toggle" member to selection of a single state from a limited number of states. Rather, the term "toggle" is intended to more broadly define the ability to selectively activate at least one of a plurality of states without limitation to the possible number of states of the "toggle member".

Additionally, as noted, the term "toggle member" is not intended to denote any particular structure. For instance, a toggle switch may be known in the art for selection of only one of a plurality of states of the switch. As used herein, "toggle member" is intended to encompass such switches, as well as alternatives, to the extent such switches are operative in a manner corresponding to the discussion presented herein.

In an additional aspect, a method for operating a hand-held electrical instrument to conduct electrosurgery is provided. The method includes a step of manipulating a toggle member comprising the hand-held electrosurgical instrument to effect activation of at least one operational state of the electrosurgical instrument, (e.g., to cut, coagulate, desiccate and/or fulgurate tissue utilizing a plurality of different electrosurgical signals supplied by electrosurgical equipment), and to effect emission of light from a light emitter comprising the electrosurgical instrument.

In various arrangements, the method may further include the steps of establishing a single tactile interface between a finger of a user and the toggle member of the electrosurgical instrument, and maintaining the single tactile interface throughout the manipulating step (e.g., to both effect activation of at least one operational state of the electrosurgical instrument and to effect emission of light from the light emitter). Again, the ability to maintain a single tactile interface with a toggle member, while controlling operation of an electrosurgical instrument, advantageously yields enhanced precision.

In various arrangements the manipulating step of the method may further comprise the steps of positioning the toggle member in the first position to effect activation of a first operational state of the electrosurgical instrument and/or positioning the toggle member in a second position (e.g., different than the first position) to effect activation of a second operational state of the electrosurgical instrument. Further, the method may optionally include a step of biasing the toggle member to a home position that is different than the first position and the second position, wherein the toggle member is selectively positionable from the home position to the first position and to the second position by a user, and wherein the electrosurgical instrument is in an inactive state when the toggle member is in the home position.

In at least one embodiment, the manipulating step of the method may further include positioning the toggle member in a third position (e.g., different than the first and second positions) to effect simultaneous activation of a first operational state of the electrosurgical instrument and the emission of light from the light emitter. Further, the manipulating step may optionally include the step of positioning the toggle member in a fourth position (e.g., different than the first, second and third positions) to effect simultaneous activation of a second operational state of the electrosurgical instrument and the emission of light from the light emitter.

In relation to the noted potential method steps, the toggle may be provided to be directly positionable between a home position and any one of the first position, the second position, the third position and/or the fourth position. In this regard, enhanced control and functional efficiencies may be realized.

In one arrangement, the electrosurgical instrument may include an electrosurgical electrode supportably interconnected to and extending from a first end of a handle portion of the electrosurgical instrument, wherein the manipulating step may further include one of either advancing the toggle member towards or retracting the toggle member away from the first end of the handle portion of the electrosurgical instrument to effect activation of the at least one operational state of the electrosurgical instrument. Further, the manipulating step may also include depressing the toggle member relative to the handle portion to effect the emission of light.

In various embodiments, the method may further include the step of illuminating a majority of a volume extending from a first end of a handle portion of the electrosurgical instrument in a direction towards a distal end of an electrosurgical electrode supportably interconnected to and extending away from the first end of the handle portion. In this regard, illumination may be realized in the volume at predetermined light levels consistent with those noted hereinabove.

In some implementations, the illuminating step may comprise emitting light from a plurality of locations at the first end of the handle portion of the electrosurgical instrument in a direction towards the distal end of the electrosurgical electrode. In some implementations, the emitting step may comprise powering a plurality of light sources, each of the plurality of light sources being disposed at different ones of the plurality of locations.

In one approach, powering of the light sources may comprise supplying an electrical signal from at least one power storage device comprising the electrosurgical instrument (e.g., one or more batteries). As may be appreciated, such electrical signal supply may be provided and controlled in conjunction with the manipulating step.

Various additional method implementations and options may be realized utilizing different ones of the features noted above in relation to embodiments of an improved hand-held electrosurgical instrument. Still further features of an improved electrosurgical instrument and related method will be appreciated upon consideration of the embodiment descriptions provided hereinbelow.

BRIEF DESCRIPTION OF THE DRAWINGS

FIG. 2 is a perspective view of an embodiment of an electrosurgical instrument showing potential illumination fields of a light emitter of the electrosurgical instrument.

DETAILED DESCRIPTION

Figure 1A:
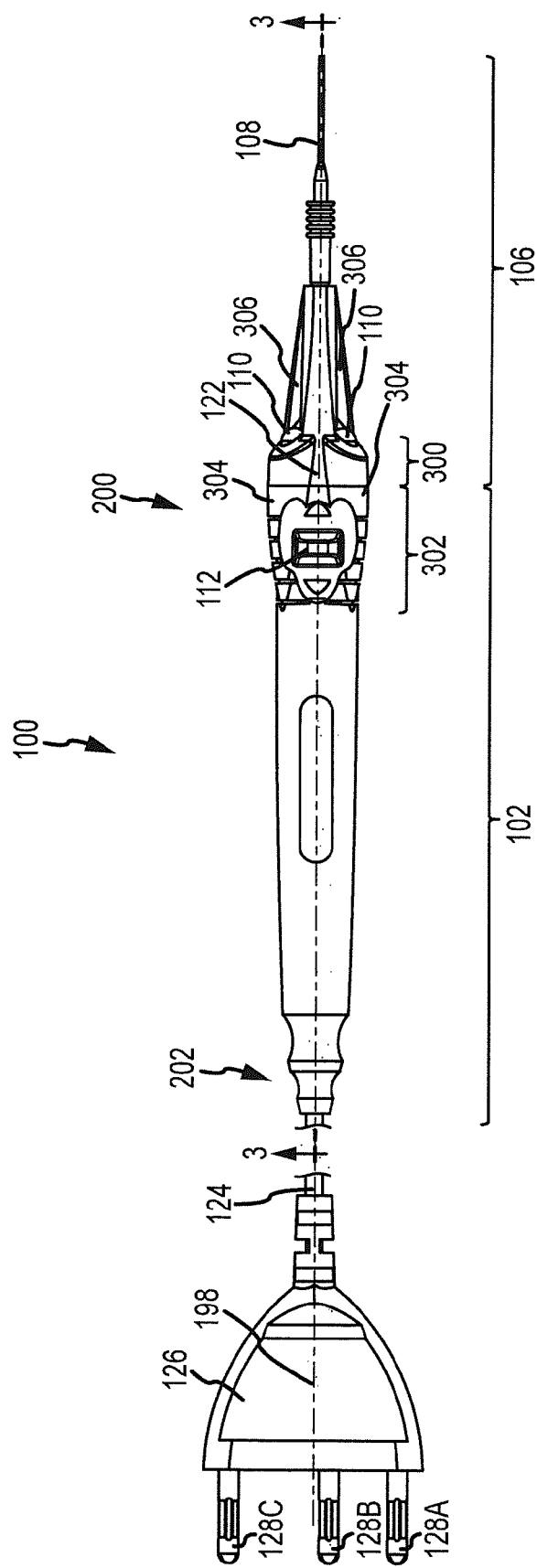
FIG. 1A is a top view of an embodiment of an electrosurgical instrument.
Figure 1B:
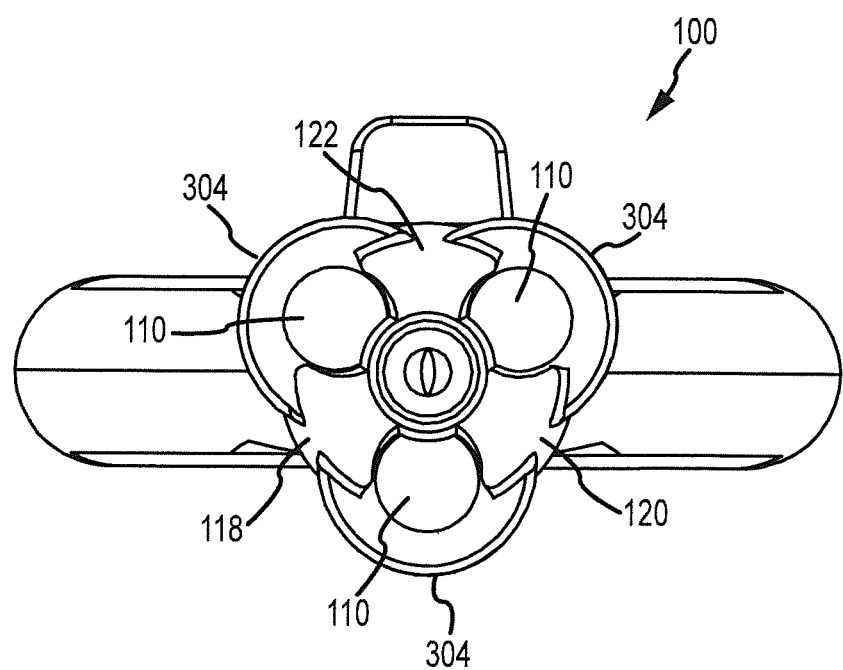
FIG. 1B is a front view of the embodiment of FIG. 1A.
Figure 1C:
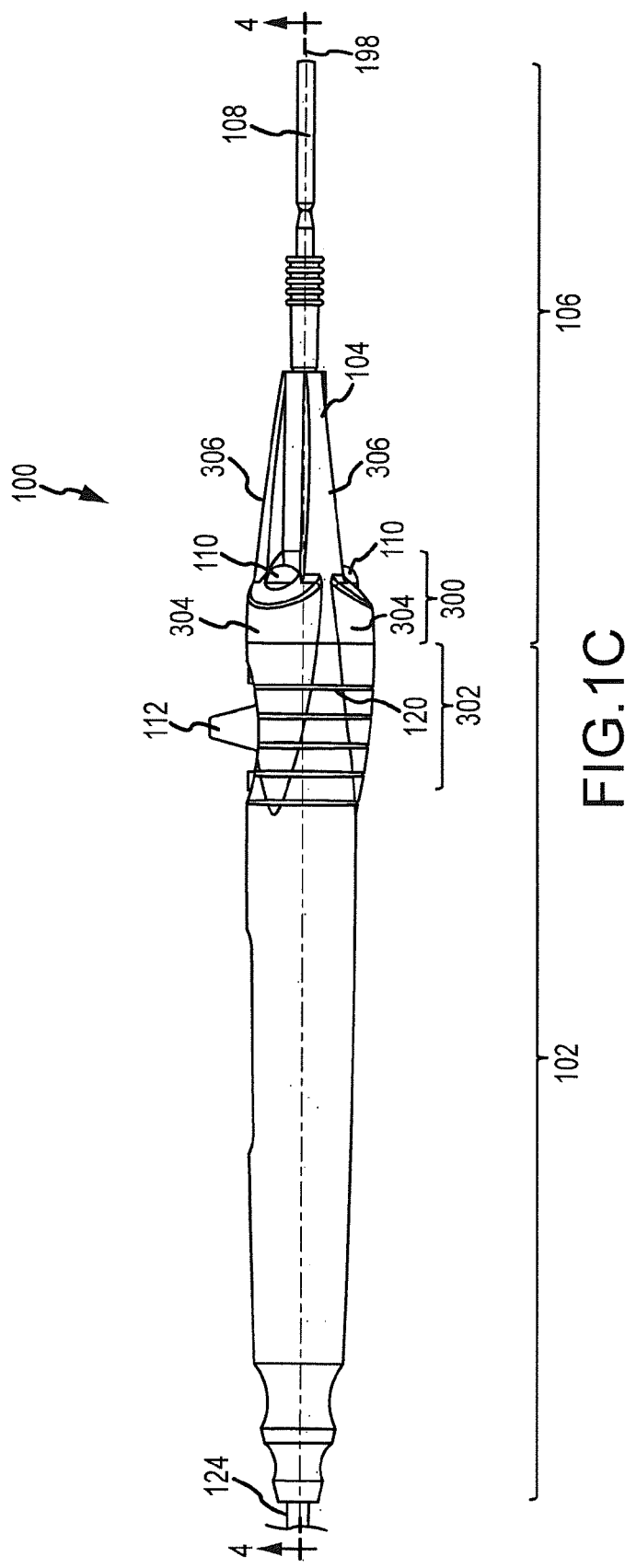
FIG. 1C is a side view of the embodiment of FIG. 1A.
Figure 1D:
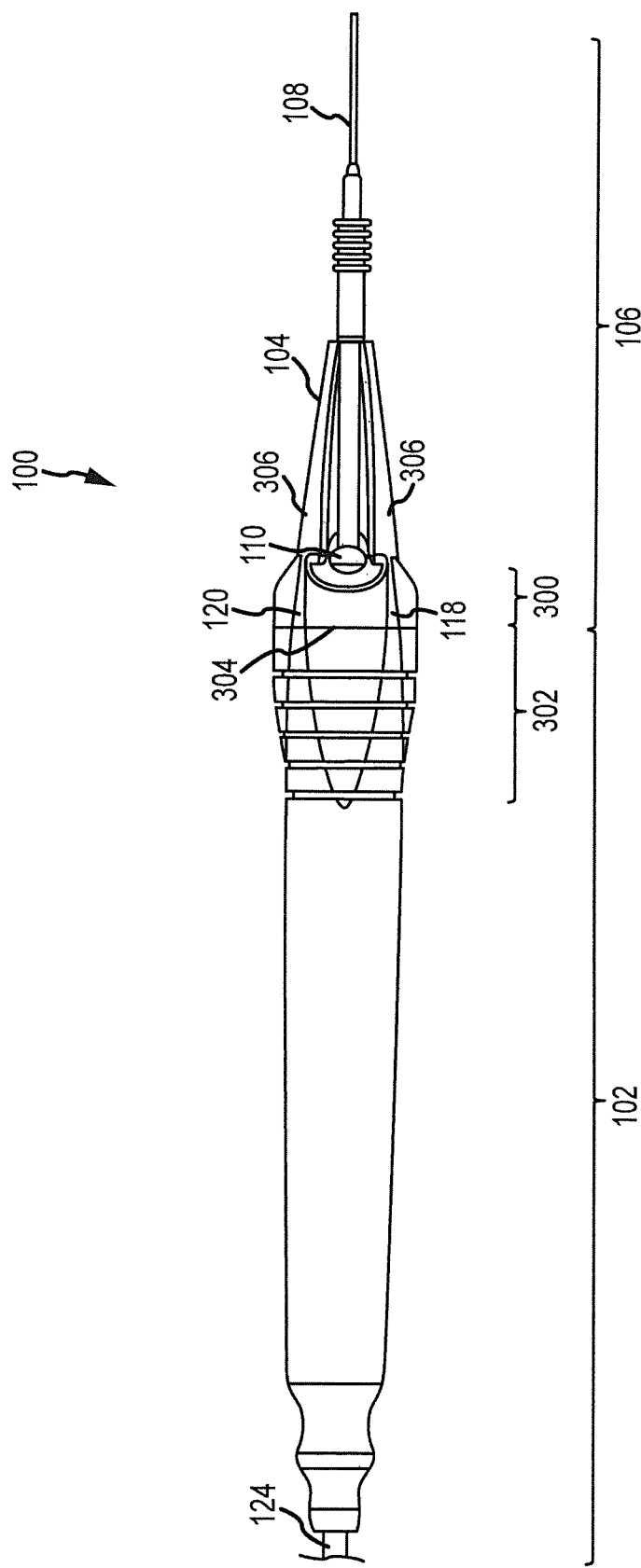
FIG. 1D is a bottom view of the embodiment of FIG. 1A.

The present invention may be implemented in configurations and alternative forms. Specific embodiments are presented herein by way of example. It should be understood that such embodiments are not intended to limit the invention to the particular form disclosed.

FIGS. 1A-1D depict various views of an embodiment of a hand-held electrosurgical instrument 100. The electrosurgical instrument 100 may include a handle portion 102. An electrosurgical electrode 106 may extend distally from a distal end 200 of the handle portion 102. Also, at least one light emitter(s) 300 may be disposed adjacent to a distal end 200 of the handle portion 102. The light emitter(s) 300 may be operative to emit light from at least one corresponding light emission location in a direction distally with respect to the handle portion 102. The light emitter(s) 300 and the electrosurgical electrode 106 may be supportably interconnected to the handle portion 102.

The handle portion 102 may comprise an elongate member extending along a longitudinal axis 198. The handle portion 102 may have a distal end 200, as referenced above, and a proximal end 202. The distal end 200 of the handle portion 102 may include a contoured segment 302. The contoured segment 302 may be configured to restrict rolling of the electrosurgical instrument 100 about the longitudinal axis 198 when resting on a support surface (e.g., an operating room table, the patient, etc.).

For instance, moment forces may be imparted on the electrosurgical instrument 100 that may cause the electrosurgical instrument 100 to roll about the longitudinal axis 198 when resting on a support surface. For a substantially cylindrical electrosurgical instrument, this may result in the generally cylindrical electrosurgical instrument rolling to an undesirable location, the electrosurgical instrument falling from the surface, or a control surface of the electrosurgical instrument contacting the support surface such that the electrosurgical instrument is inadvertently activated.

The contoured segment 302 of the electrosurgical instrument 100 may have at least one substantially flattened side (e.g., defined by at least two spaced peripheral regions extending along the configured segment and disposed in a common tangent plane) that may allow the electrosurgical instrument 100 to come to rest on that substantially flattened side and resist moment forces imparted onto the electrosurgical instrument 100.

For example, the embodiment depicted in FIGS. 1A-1D includes a first side 118, a second side 120, and a third side 122 arranged in a generally triangular configuration and extending along the contoured segment 302 of the distal end 200 of the handle portion 102. The first side 116, the second side 118, and the third side 122 may be defined as substantially flattened surfaces extending between two corresponding surface projections 304. Each of the surface projections 304 may generally comprise a conical, elliptical, or parabolic projection which tapers proximally along the length surface projection 304 as shown in FIGS. 1A-1D. In this regard, the surface projections 304 of the illustrated embodiment may taper toward the longitudinal axis 198 of the handle portion 102 in a proximal direction as shown.

In any regard, adjacent pairs of surface projections 304 may define corresponding ones of the first side 118, second side 120, or third side 122, therebetween. The first side 118 and the second side 120 may be disposed directly adjacent to each other and may intersect at a vertex corresponding to one of the surface projections 304. The third side 122 may be provided adjacent to both the first side 118 and second side 120 and intersect the first side 118 and the second side 120 at respective vertices adjacent to corresponding surface projections 304. In this regard, the generally triangular configuration of the contoured portion 302 may be operative to resist a moment force acting on the electrosurgical instrument 100, thus reducing the likelihood that the electrosurgical instrument 100 will roll about the longitudinal axis 198.

In the particular embodiment depicted in FIGS. 1A-1D, the triangular shape defined by the first side 118, second side 120, and third side 122, may help prevent the electrosurgical instrument 100 from rolling in excess of 60 degrees regardless of how in the electrosurgical instrument 100 comes to rest on a support surface. For example, in the case were the vertex of the first and second side 118 and 120 contacts a surface, the instrument may only roll at most 60 degrees in either direction prior to coming to rest on one of the first or second side 118 or 120. Accordingly the likelihood of adverse outcomes associated with a rolling electrosurgical instrument may be reduced.

Additionally, the first side 118, second side 120, and third side 122 may coordinate to define one or more control surfaces. For instance, in the depicted embodiment, a corresponding one of a user's fingers may come to rest on a respective one of the sides. In this regard, the contoured segment 302, in addition to assisting in preventing rolling of the electrosurgical instrument 100, may also provide an ergonomically shaped control surface to coordinate with a user's fingers. As such, control over the electrosurgical instrument 100 may be improved.

As briefly described above, the light emitter(s) 300 may be disposed adjacent to the distal end 200 of the handle portion 102. For instance, the light emitter(s) 300 may be supportably interconnected to the distal end 200 of the handle portion 102. The light emitter(s) 300 may be operative to emit light from one or more corresponding light emission locations in a direction distal to the distal end 200 of the handle portion 102. For example, the light emission locations may be spaced about the periphery of the handle portion 102 at the distal end 200 thereof. The plurality of light emission locations may correspond with (e.g., be aligned with) the surface projections 304 which define the respective sides of the electrosurgical instrument 100 along the contoured segment 302. In this regard, the light emission locations of the light emitter 300 may be disposed adjacent to one or more of the vertices of two adjacent sides defined by a corresponding surface projection 304.

The light emitter(s) 300 may comprise at least one light source or a plurality of light sources. For example, a plurality of light sources may be supportably interconnected to the handle portion 102 adjacent to each respective one of the plurality of light emission locations. In one embodiment, the light sources may include one or more light emitting diode (LED).

In the embodiment depicted in FIGS. 1A-1D, the light emitter(s) 300 may be defined by a plurality of LED light sources 110 disposed adjacent to the distal end 200 of the handle portion 102. The light sources 110 may be disposed so as to emit light in a direction distal to the handle portion 102.

With reference to FIG. 2, at least a portion of the light emitted distally from the light sources 110 may illuminate at least a portion of a volume 252 extending distally from the light sources 110 with respect to the handle portion 102 along the length of an electrosurgical electrode 106. As shown, the volume 252 may be of a generally conical or frustoconical shape extending from the light emitter(s) 300 distally with respect to the handle portion 102.

Since the volume 252 may at least partially surround the electrosurgical electrode 106, light emitted from the light sources 110 may advantageously illuminate the a relatively large surgical field of interest adjacent to where the electrosurgical electrode 106 interfaces with a patient. While one particular shape of the volume 252 is depicted, it will be understood that the shape and size of the volume 252 may be varied. For instance, light sources 110 having different light emission properties (e.g., varying power consumption, light intensities, emission angles, etc.) may be used to vary the shape and size of the volume 252 extending distally from the light emitter 300. In any regard, as the light sources 110 are generally provided distally on the handle portion 102 of the electrosurgical instrument 100, light emitted from the light sources 110 may be cast onto the surgical field of interest such that the appearance of shadows on the surgical field is reduced.

In one embodiment, the light sources 110 may illuminate at least a majority of the volume 252 with at least 1000 millicandela (mcd) of light. In another embodiment, adding additional light sources 110 may illuminate at least a majority of the volume 252 with at least 2000 mcd of light, at least 3000 mcd of light or even at least 5000 mcd of light. Each one of the light sources 110 may emit light the same wavelength or at corresponding different predetermined wavelengths. In one embodiment, the light sources 110 may emit light of a color temperature approximating incandescent or greater. For instance, the color temperature may be about 3000 K or greater.

The electrosurgical instrument 100 may also include a power source, e.g., one or more power storage device(s) such as one or a plurality of batteries. The power source may be in selective electrical communication with the light emitter(s) 300. In that regard, electrical communication between the power source and the light emitter(s) 300 may be controlled to selectively activate the light emitter(s) 300 so as to emit light from the light emission locations distally with respect to the handle portion 102.

Figure 3:
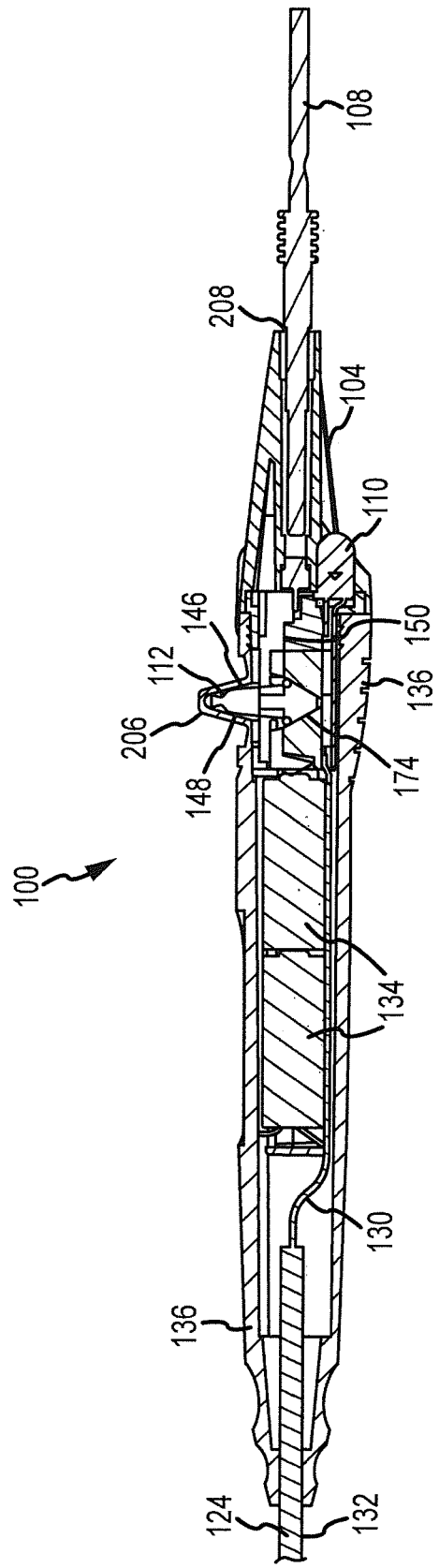
FIG. 3 is a cross sectional view of the embodiment shown in FIG. 1A taken along section line 3-3 in FIG. 1A.
Figure 4:
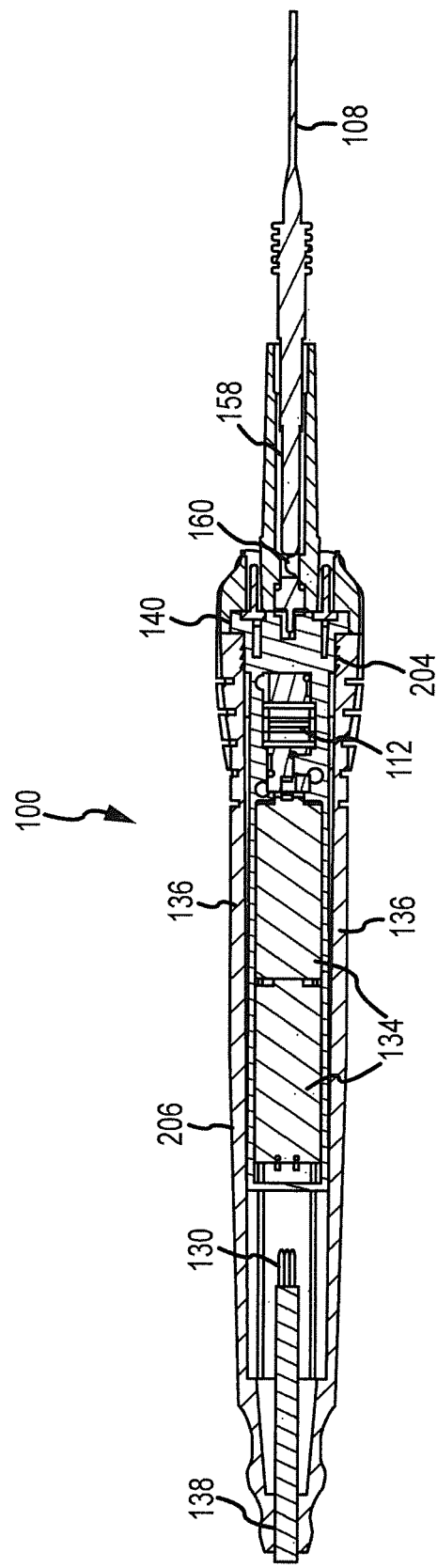
FIG. 4 is a cross sectional view of the embodiment shown in FIG. 1C taken along section line 4-4 in FIG. 1C.

As shown in FIGS. 3 and 4, the power source may include one or more batteries 134 (e.g., two batteries 134 provided in a series or parallel arrangement). In this regard, at least a portion of a lighting circuit, as discussed in greater detail below, may be supportably connected to the handle portion 102 to selectively activate the light emitter(s) 300 to emit light from the light emission locations.

Alternatively, a power source may be disposed remotely from the handle portion 102 to provide power to the light emitter(s) 300, which, as described above, may be provided with the handle portion 102 or also disposed remotely from the handle portion 102. For instance, the power source may be an external battery pack located remotely from the handle portion 102, or power may be delivered via cable from the electrosurgical generator. The power source may thus be in electrical communication with the electrosurgical instrument 100, for example, by way of a wire or additional cable (e.g., extending within an existing signal cable 124).

As noted above, the electrosurgical instrument 100 may include an electrosurgical electrode 106 extending distally from a distal end 200 of the handle portion 102. The electrosurgical electrode 106 may have a bipolar configuration, a monopolar configuration, a sesquipolar configuration, or may be any other appropriate type of electrosurgical electrode 106. The electrosurgical electrode 106 may include a metallic electrode conductor 108 of any appropriate type. The electrosurgical electrode 106 may be in operative communication with electrosurgical equipment (e.g., an electrosurgical generator) (not shown in FIGS. 1A-1D) such that the electrosurgical equipment may be operable provide an electrosurgical signal to the electrode conductor 108 of the electrosurgical electrode 106. In this regard, at least one operational state of the electrosurgical instrument 100 may be activated to perform an electrosurgical operation using the electrosurgical instrument 100.

At least a portion of the electrode conductor 108 may be in selective electrical communication with one or more electrosurgical paths 130, which are in electrical communication with the electrosurgical equipment. For instance, in the embodiment depicted in FIGS. 3 and 4, the electrode conductor 108 may be retained in an electrode socket 158. The electrode socket 158 may be supportably interconnected to the handle portion 102. The electrode socket 158 is conductive which establishes electrical communication between the electrode conductor 108 and a selected electrosurgical path 130 as will be discussed in greater detail below.

Additionally, the electrode conductor 108 may be removably disposed with respect to the electrode socket 158. Accordingly, the electrode conductor 108 may be removed from the electrode socket 158 and replaced with one or more alternate electrode conductors. As such, different styles of electrode conductors 108 (e.g., blades, paddles, needles, snares, etc.) may be interchangeably fitted into the electrode socket 158. Additionally, the electrode conductor 108 may be rotated in the electrode socket 158. As such, the electrode conductor 108 may be positioned and retained by friction at different angular positions with respect to the electrode socket 158.

In the illustrated embodiment in FIGS. 1A-1D, a signal cable 124 may extend proximally from the proximal end 202 of the handle portion 102. The signal cable 124 may terminate in a plug body 126. The plug body 126 may include plurality of connectors 128A, 128B, and 128C, which extend from the plug body 126. The plug body 126 and connectors 128A-128C may be configured so as to establish electrical communication between corresponding electrosurgical paths 130 and the electrosurgical equipment (e.g., electrosurgical paths 130A-130C described below in relation to FIG. 5). In this regard, the shape and arrangement of the plug body 126 and connectors 128A-128C may correspond to an appropriate receiver on the electrosurgical equipment. That is, the shape and arrangement of the plug body 126 and connectors 128A, 128B, and 128C may comprise a standard electrosurgical connection or a proprietary electrosurgical connection corresponding to a particular type of electrosurgical equipment.

The electrosurgical instrument 100 may further include a toggle member 112. The toggle member 112 may be operative to control various aspects of the electrosurgical instrument 100. For instance, the toggle member 112 may be operative to selectively control light emission from the light emitter(s) 300. Additionally, and/or alternatively, an operational state of the electrosurgical instrument 100 may be selectively controllable by the toggle member 112. Accordingly, the toggle member 112 may be manipulated to different positions to selectively activate different operational states of the electrosurgical instrument 100 and/or control emission of light from the light emitter 300. In alternative embodiments, the toggle member 112 may include a foot switch to control the operational states of the electrosurgical instrument. In such embodiments, a finger toggle may still be provided with the electrosurgical instrument 100 to control the selectively emission of light therefrom.

In one embodiment, the toggle member 112 may present a single tactile interface point that is manipulatable by a user (e.g., a surgeon) to control the operational state of the electrosurgical instrument 100 as well as to control the emission of light from the light emitter 300. In contrast, many electrosurgical instruments include separate interface points disposed at different locations on the electrosurgical instrument for control of the activation of individual features of the electrosurgical instrument. For example, to utilize such instruments, a user must remove his or her finger from a first button, shift the position of the finger with respect to the electrosurgical instrument, and replace the finger on the electrosurgical instrument to activate the other of the buttons to activate a different state of the electrosurgical instrument. The removal and repositioning of the user's finger may result in inconsistent pressure and may reduce the ability to control the electrosurgical instrument during the time the finger is removed from the instrument. Additionally, shifting a finger with respect to the electrosurgical instrument may cause the instrument to pitch in an undesired direction. Consequently, the accuracy of the user's movements may be diminished as a neuro-surgery.

In the electrosurgical instrument 100, the toggle member 112 allows for constant contact with a single tactile interface point while selectively changing the operational state of the electrosurgical instrument 100 and/or the emission of light. In turn, activation of the various features of the electrosurgical instrument 100 does not require the user to remove his or her finger from the electrosurgical instrument 100. As a result, control of the instrument may be maintained, undesired pitching of the instrument associated with the shifting of the location of the user's finger with respect to the instrument may be avoided, and consistent pressure may be applied. In turn, the accuracy of the user's movements may be maintained even when changing between operational states of the electrosurgical instrument 100.

Figure 5:
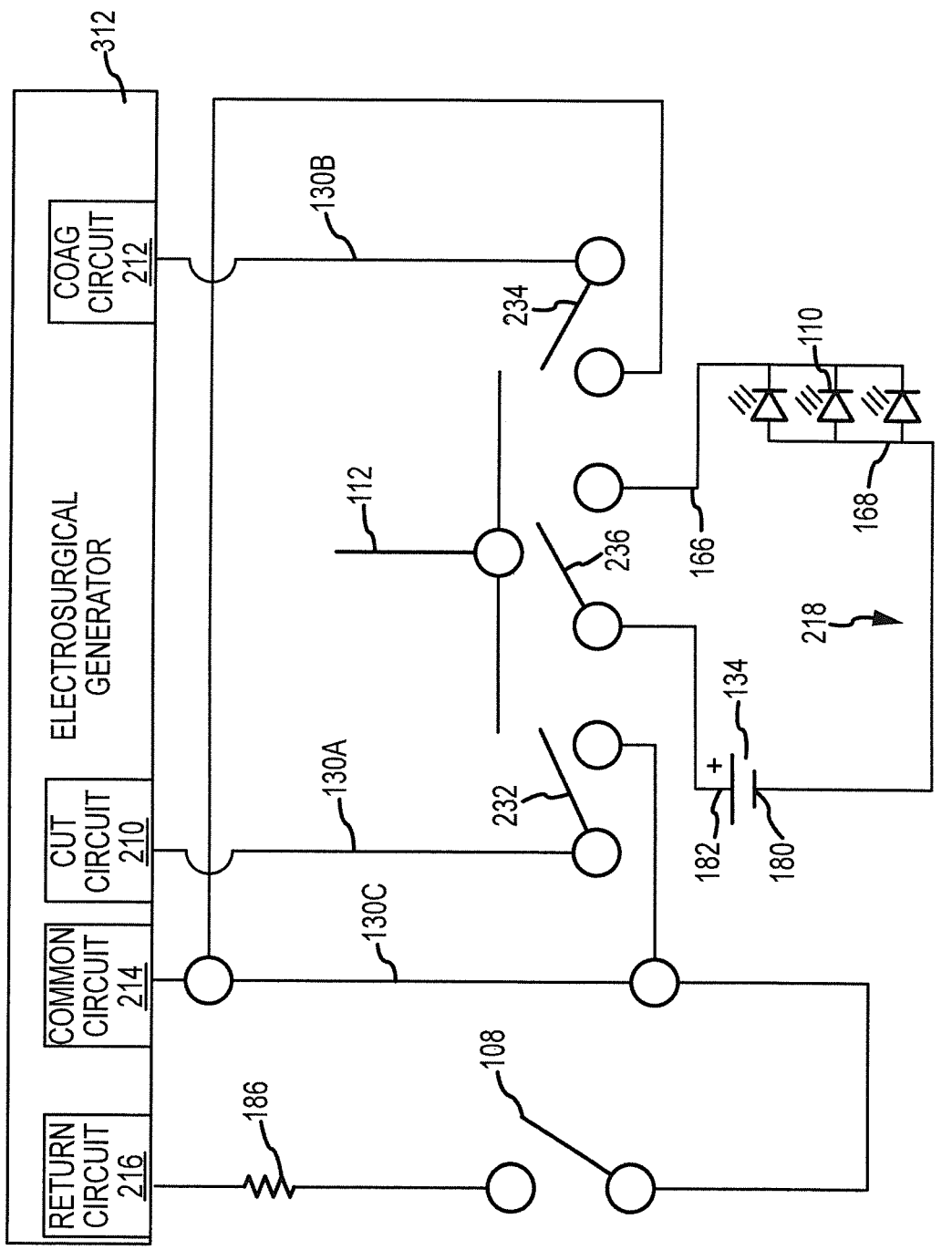
FIG. 5 is a circuit diagram of an embodiment of an electrosurgical instrument.

A diagram depicting an embodiment of a circuitry design comprising a plurality of electrosurgical paths 130 and an embodiment of a lighting circuit 218 for the instrument 100 is shown in FIG. 5. As previously stated, the handle portion 102 may include a number of electrosurgical paths 130 that are selectively engageable to selectively supply an electrosurgical signal to the electrosurgical electrode 106. Additionally, the handle portion 102 may include a lighting circuit 218, whereby electrical power may be selectively applied to activate a light source resulting in emission of light from the light emitter 300.

FIG. 5 includes electrosurgical equipment comprising an electrosurgical generator 312. The electrosurgical generator 312 may have an electrosurgical cut circuit 210 and an electrosurgical coag circuit 212. The cut circuit 210 and coag circuit 212 may produce different waveforms specific to a cut operation and a coag operation, respectively. The cut circuit 210 may be in electrical communication with a first electrosurgical path 130A (e.g., by way of the connector 128A shown in FIGS. 1A-1D, 3, and 4). The coag circuit 212 may be in electrical communication with a second electrosurgical path 130B (e.g., by way of the connector 128B shown in FIGS. 1A-1D, 3, and 4). The electrosurgical generator 312 may also have an electrosurgery common circuit 214. The common circuit 214 may be in electrical communication with a third electrosurgical path 130C (e.g., by way of the connector 128C shown in FIGS. 1A-1D, 3, and 4). The electrosurgical paths 130A, 130B, and 130C may be defined by a wire, a trace, other conductive element, or any combination of the foregoing.

The first electrosurgical path 130A may be in electric communication with a first contact of a cut switch 232. The third electrosurgical path 130C may be in electrical communication with a second contact of the cut switch 232. Upon closing of the cut switch 232, the cut circuit 210 and common circuit 214 may close and the cut waveform may be activated at the electrode conductor 108. The second electrosurgical path 130B may be in electric communication with a first contact of a coag switch 234. The third electrosurgical path 130C may be in electrical communication with a second contact of the coag switch 234. Upon closing of the coag switch 234, the coag circuit 212 and common circuit 214 may close and the coag waveform may be activated at the electrode conductor 108.

The electrode conductor 108 is represented as a switch in FIG. 5. Thus, when an operational state of the electrosurgical instrument 100 is active and upon contact or near contact of the electrode conductor 108 with the patient 186, current may flow through the electrode conductor 108 to the patient 186 to perform an electrosurgical operation adjacent to the electrode conductor 108. The patient 186 may be connected to the electrosurgical generator 312 by way of a return circuit 216 (e.g., a grounding pad, grounded operating room table, etc.). In turn, electrical current passing through the electrode conductor 108 may flow through the patient to the return circuit 216.

Additionally, FIG. 5 depicts a lighting circuit 218, which may be used to selectively activate the light emitter(s) 300 (e.g., light sources 110 as depicted in FIG. 5). The lighting circuit 218 may also have a light switch 236 which is operative to open and close the lighting circuit 218. Upon closing of the light switch 236, the lighting circuit 218 may be activated to activate the light source (e.g., light sources 110). Thus, the toggle member 112 may be disposed in a position that closes the lighting switch 236 to activate the light sources 110.

The lighting circuit 218 may include one or more batteries 134 arranged in a series or parallel circuit. The positive terminal 182 of the battery may be in electrical communication with a first contact of the light switch 236. The positive leads 166 of each of the light sources 110 may be in electrical communication with a second contact of the light switch 236. The light sources 110 may be provided in a series or parallel lighting circuit 218. The negative leads 168 of the light sources 110 may be in electrical communication with the negative terminal 180 of the batteries 134.

In the illustrated embodiment, the toggle member 112 may have five positions. While these positions are referenced herein as the first through the fifth position, this is for demonstrative purposes only and is not intended to connote any sequence of positions. In this regard, any of the first through fifth positions may be selected in any order without the toggle member 112 passing through any intermediate position to arrive at any given position. That is, any of the positions may be randomly, non-sequentially selected.

In a first position, the toggle member 112 may contact the cut switch 232 to close the cut switch 232. Accordingly, the first position may activate the cut operation of the electrode conductor 108 as the first electrosurgical path 130A and the third electrosurgical path 130C are in turn electrically connected. A second position of the toggle member 112 may contact the coag switch 234 to close the coag switch 234. Accordingly, the second position may activate the coag operation of the electrode conductor 108 as the second electrosurgical path 130B and the third electrosurgical path 130C are in turn electrically connected. A third position of the toggle member 112 may make contact with the cut switch 232 as well as the light switch 236. As such, the cut operation of the electrode conductor 108 may be activated and the light sources 110 may be illuminated. A fourth position of the toggle member 112 may contact the coag switch 234 as well as the light switch 236. Accordingly, the coag operation of the electrode conductor 108 may be activated and the light sources 110 may be illuminated. A fifth position of the toggle member 112 may result in the toggle member 112 only contacting the light switch 236 to close the light switch 236. As such, only the light sources 110 may be illuminated, while no electrosurgical circuit is established.

With further reference to FIGS. 3 and 4, the connectors 128A-128C of the plug body 126 may be operatively interconnected to a respective one of the electrosurgical paths 130 which are contained within an insulative cover 132 of the signal cable 124 along substantially all of the length of the signal cable 124. The electrosurgical paths 130 may in turn be in operative communication with a circuit member 150. The circuit member 150 may interact with the toggle member 112 to selectively establish electrical communication between one or more of the electrosurgical paths 130 to activate at least one operational state of the electrosurgical instrument 100. In this regard, various electrosurgical operations (e.g., a cut operation, coag operation, etc.) facilitated by the various electrosurgical paths 130 may be activated using the toggle member 112.

In the particular embodiment illustrated in FIGS. 3 and 4, the toggle member 112 may have a first leg 146 and a second leg 148, each of which is in contact with a toggle receiver 174. The toggle receiver 174 may comprise a portion of a handle chassis 204 and circuit member 150. The handle chassis 204 may be a substantially rigid member which extends along the longitudinal axis 198 of the instrument 100 and comprises a portion of the handle portion 102.

The toggle receiver 174 may include inclined side walls along which the first and second leg 146 and 148 may be positioned. The first leg 146 and second leg 148 may be biased in a spaced apart position. Accordingly, the toggle member 112 may interact with the toggle receiver 174 such that the legs 146 and 148 of the toggle member 112 are urged toward the most spaced apart portion of the toggle receiver 174.

The handle portion 102 comprises an elastomeric material which defines an elastomeric handle portion 136 and includes a correspondingly shaped pocket 206 to receive a portion of the toggle member 112. The pocket 206 of the elastomeric handle portion 136 may help to retain the toggle member 112 in the toggle receiver 174 at the uppermost level thereof as shown in FIG. 2. Additionally or alternatively, a ledge 220 (shown in FIG. 6) may be provided to retain the toggle member 112 in contact with the circuit member 150 at the most spaced apart portion of the toggle receiver 174. The pocket 206 may also maintain the toggle member 112 in a centered position with respect to the toggle receiver 174. This position, shown in FIG. 2 wherein the toggle member 112 is centered with respect to the toggle receiver 174 and residing at the most spaced apart portion of the toggle receiver 174 sidewalls, may be referred to as a home position. When the toggle member 112 is in the home position, the lighting circuit and the electrosurgical circuits may be inactive. As discussed below, the toggle member 112 may be manipulatable away from this home position to activate at least one of the electrosurgical circuits and/or the lighting circuit.

Figure 6:
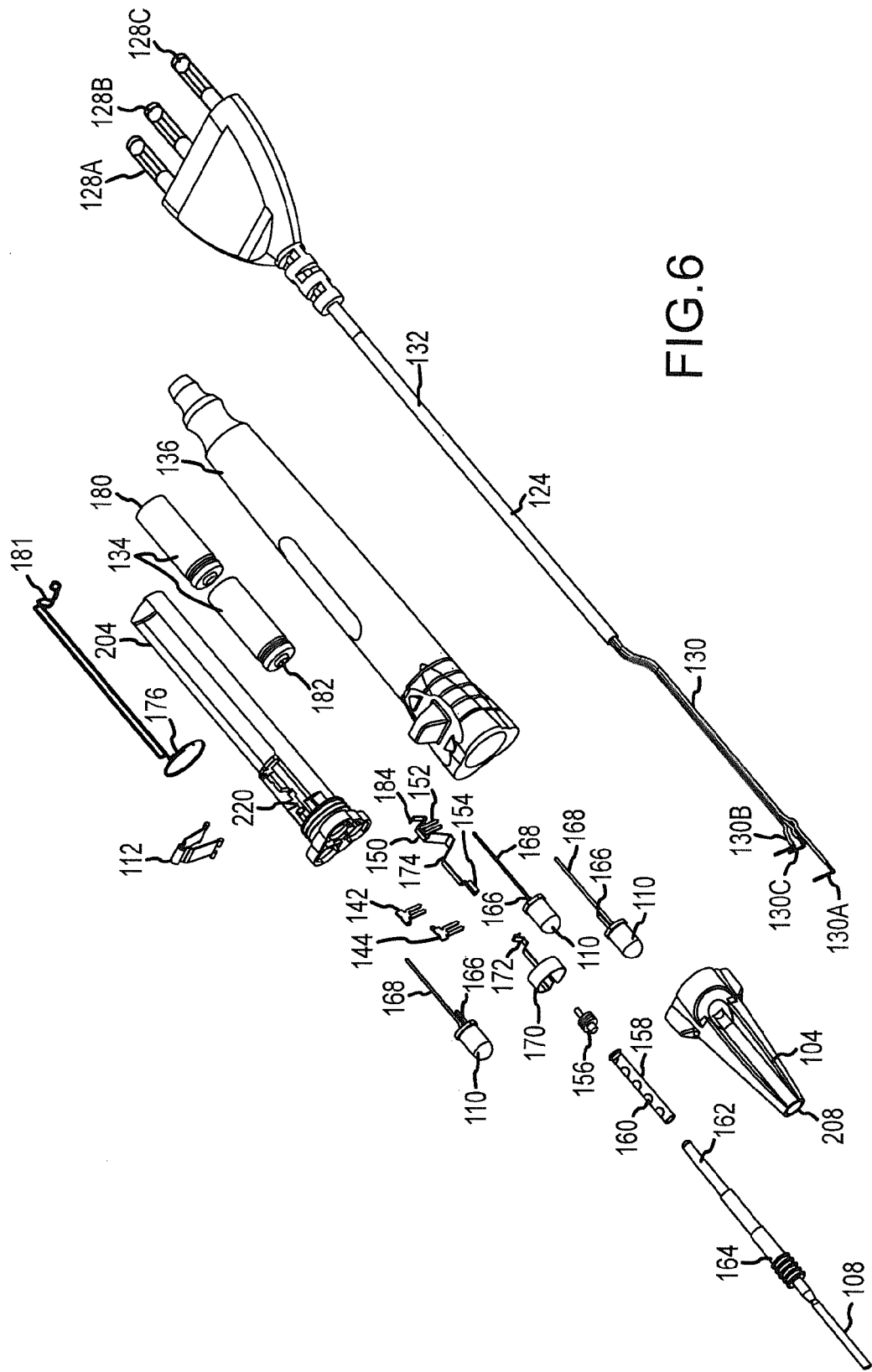
FIG. 6 is an exploded view of an embodiment of an electrosurgical instrument.

With reference now to FIG. 6, an exploded view of the embodiment depicted in FIGS. 1A-1D, 3, and 4 is shown. A signal cable 124 may be provided that contains a portion of the electrosurgical paths 130A, 130B, and 130C. The signal cable 124 may also include an insulative covering 132 through which the electrosurgical paths 130A, 130B, and 130C pass. In this regard, connector 128A may be in electrical communication with the first electrosurgical path 130A. Similarly, the connector 128B may be in electrical communication with the second electrosurgical path 130B, and connector 128C may be in electrical communication with the third electrosurgical path 130C.

The first electrosurgical path 130A may be in electrical communication with a cut contact 144. The second electrosurgical path 130B may be in electrical communication with a coag contact 142. The cut contact 144 and coag contact 142 may be disposed on opposite sides of the toggle member 112 and selectively contactable by respective legs 146 and 148 the toggle member 112, as will be discussed in further detail below. The electrosurgical common circuit corresponding to the third electrosurgical path 130C may be in electrical communication with the circuit member 150. The circuit member 150 may comprise a conductive body. The circuit member 150 may include a common contact 152 which is in electrical communication with the third electrosurgical path 130C. The respective electrosurgical paths 130A-130C may, for instance, be pressed into contact with a respective one of the contact members 142, 144, and 152 to establish electrical communication therewith.

Additionally, the circuit member 150 may also have an electrode contact 154 which, when the instrument 100 is assembled, contacts a socket pin 156. The socket pin 156 is in further electrical communication with the conductive electrode socket 158. An aperture 208 of a nose 104 may receivingly engage a proximal end 162 of the electrode conductor 108. As such, the electrode socket 158 provided on the interior of the nose 104 may establish electrical communication between the socket pin 156 and the proximal end 162 of the electrode conductor 108.

An electrode insulator 164 may be disposed about the electrode conductor 108 to provide electrode isolation thereof and may allow for gripping to remove or rotate the electrode conductor 108. The electrode isolator 164 may be slidingly received by the aperture 208 in the nose 104 to further supportably connect the electrode conductor 108. As the electrode conductor 108 may be slidingly received by the electrode socket 158 and nose 104, the electrode conductor 108 may be rotatable in the electrode socket 158 to different angular positions or may be removed and replaced with alternate electrodes. A center axis of the electrode conductor 108 may in turn be aligned with the longitudinal axis 198 of the handle portion 102.

Each light source 110 may include a positive lead 166 and a negative lead 168. The negative lead 168 may extend a greater distance proximately than the positive lead 166 for each of the light sources 110. In this regard, each of the positive leads 166 of the light sources 110 may be in electrical communication with a light source connector ring 170. The light source connector ring 170 may include a toggle contact surface 172 which, when the instrument is assembled, may be aligned with a toggle receiver 174 provided on the circuit member 150. The toggle contact surface 172 may be positioned adjacent to the toggle receiver 174 and be in selective electrical communication with the toggle receiver 174 by way of manipulation of the toggle member 112. The toggle contact surface 172 may correspond to the inclined side walls of the toggle receiver 174. The negative leads 168 of the light sources 110 may be electrically isolated from the light source connector ring 170 and may extend distally to contact a light connector 176. The light connector 176 may include a lead contact ring 178 in electrical communication with the negative lead 168 of the light sources 110. A battery contact 180 may be provided on a proximal end of the light connector 176. The battery contact 180 may be provided in contact with a negative terminal 180 of at least one battery 134 supportably interconnected to the handle chassis 204. As shown, two batteries 134 are provided in series and may be disposed in the handle chassis 204 when the instrument 100 is assembled. Alternatively, the two batteries 134 may be provided in parallel. The positive terminal 182 of the battery 134 or batteries may contact a positive battery contact 184 provided on a proximal end of the circuit member 150.

As shown in FIGS. 4 and 6, the elastomeric handle portion 136 may comprise and extend along substantially all of the handle portion 102. The elastomeric handle portion 136 may form a distal annular seal 140 that may press against a corresponding annular surface of the handle chassis 204 to prevent introduction of fluids into the interior of the elastomeric handle portion 136. Additionally or alternatively, an adhesive or the like may be applied at the interface between the elastomeric handle portion 136 and the annular surface of the handle chassis 204 to provide a permanent distal annular seal 140.

In this regard, any portion of the electrosurgical paths 130 and/or lighting circuit 218 contained in the elastomeric handle portion 136 may remain isolated from fluids (e.g., bodily fluids in contact with the electrosurgical instrument 100 during a procedure, saline introduced to a wound area during a procedure, etc.). This may prevent unintentional activation of one or more of the electrosurgical circuits or lighting circuit due to an electrical short caused by ingress of conductive fluids and may also electrically isolate a user or patient from the circuitry provided in the electrosurgical instrument 100.

Further in this regard, the elastomeric handle portion 136 may extend continually from the proximal end 202 of the handle portion 102 to the distal end 200 of the handle portion 102. The elastomeric handle portion 136 may form a proximal annular seal 138 adjacent to the proximal end 202. The proximal annular seal 138 may be disposed adjacent to where the signal cable 124 meets the handle portion 102. As such, the elastomeric handle portion 136 may press against the insulative covering 132 to form the proximal annular seal 138. Additionally or alternatively, an adhesive or the like may be applied at the interface between the elastomeric handle portion 136 and the insulative covering 132 of the signal cable 124 to provide a permanent proximal annular seal 138.

The elastomeric handle portion 136 may extend in a continuous manner distally from the proximal end 202 of the handle portion 102. The elastomeric handle portion 136 may be correspondingly contoured to the exterior of the handle chassis 204 along the interior surface of the elastomeric handle portion 136. The elastomeric handle portion 136 may provide a gripping surface 206 along the exterior of the elastomeric handle portion 136. The gripping surface 206 may be finished so as to provide a slip resistant surface. This slip resistant surface, along with the elastomeric nature of the elastomeric handle portion 136 may provide a suitable gripping surface for a user to manipulate the instrument 100. The elastomeric handle portion 136 may include a contoured portion 302 accommodating and/or partially defining the surface projections 304.

The elastomeric handle portion 136 may extend continuously over the toggle member 112 so as to define a seal adjacent to the toggle member 112. Therefore, the elastomeric handle portion 136 may facilitate deflection of the toggle member 112 from the home position while maintaining the seal adjacent to the toggle member 112. As such, the toggle member 112 may be allowed to deflect with respect to the handle chassis 204 such that the elastic deflection of the elastomeric handle portion 136 maintains a seal adjacent to the toggle member 112. This, in addition to the foregoing discussion regarding the sealing of the elastomeric handle portion 136 at the proximal end 202 and distal end 200, may effectively include the ingress of fluids into the interior of the elastomeric handle portion 136 so as to maintain electrical isolation of the electrosurgical paths and lighting circuit, and to maintain electrical isolation between the electrosurgical instrument 100 and a user of the electrosurgical instrument 100.

The nose 104 may be supportably connected to and extend distally from the distal end 200 of the handle portion 102. The nose 104 may have a corresponding shape so as to define a conformal transition at the interface between the proximal end of the nose 104 and the distal end of the handle portion 102. That is, the external perimeter shape of the nose 104 may be of the same shape as the external perimeter shape of the distal end 200 of the handle portion 102. The nose 104 may generally taper along its length from the junction of the nose 104 with the distal end 200 of the handle portion 102 in a direction distal to the proximal end of the nose 104. Also, the nose 104 may include tapering ribs 306 extending from the conformal transition between the nose 104 and the handle portion 102. In this regard, each of the ribs 306 may comprise an extended surface corresponding to one of the first side 118, second side 120, or third side 122. As such, corresponding ribs 306 may coordinate with one of the first side 118, second side 120, and third side 122 to provide an extended grip surface extending along the nose 104. Accordingly, a corresponding extended grip surface comprising a rib 306 and one of the sides 118, 120, and 122 may facilitate improved control of the electrosurgical instrument 100 by a user.

In some embodiments, the nose 104 may be light transmissive, e.g., transparent or translucent. As such, the nose 104 may be operative to diffuse or refract light emitted from a corresponding light emission location of the light emitter 300 adjacent to the proximal end of the nose 104. The nose 104 may be supportably connected to the handle chassis 204. This connection of the nose 104 to the handle chassis 204 may use any appropriate joining mechanism, including press fits, adhesives, ultrasonic welding, etc. In any regard, the interface of the nose 104 and the handle portion 102 may also be sealed to prevent ingress of fluids into the interior of the handle portion 102. Additionally, the nose 104 may include one or more light openings 308 may be provided in the nose 104. Corresponding light openings 308 may be provided for each light emission location of the light emitter 300. For instance, in the embodiment depicted wherein light sources 110 define the light emitter 300, at least a portion of each of the light sources 110 may extend into a corresponding light opening 308. The interface between the light opening 308 and the light source 110 extending there through may be sealed (e.g., by way of an interference fit, adhesives, etc.).

Figure 7A:
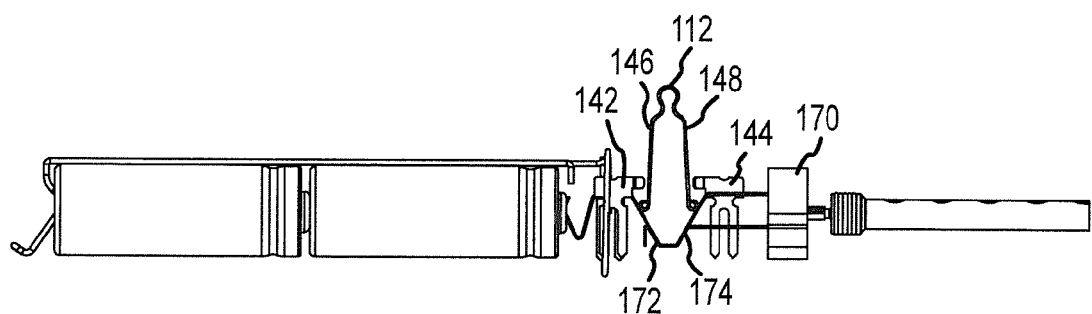
FIGS. 7A-7F are cut away views of a toggle member of an embodiment of an electrosurgical instrument in various positions.

FIGS. 7A-7F demonstrate the various positions of the toggle member in one embodiment. In FIG. 7A, the toggle member 112 may be in a home position. The first leg 146 and second leg 148 of the toggle member 112 may be resting against the toggle receiver 174 above a level where the toggle contact surface 172 is adjacently disposed. In turn, the lighting circuit may remain open and the light sources 110 may remain inactive. As previously discussed, the inclined side walls of the toggle receiver 174 may bias the toggle member 112 away from the toggle contact surface 172 at the most spaced apart portion of the inclined walls of the toggle receiver 174. For instance, in one embodiment, the toggle member 112 may be prevented from moving further away from the toggle contact surface 172 by way of the elastomeric handle portion 136. Additionally or alternatively, a ledge 220 (shown in FIG. 6) on the handle chassis 204 may be provided to limit the extent of travel of the toggle member 112 at the uppermost level of the toggle receiver 174. An elastomeric handle portion 102 may also maintain the toggle member 112 in the home position as shown in FIG. 7A by centering the toggle member 112 in the home position such that neither the first leg 146 nor second leg 148 contacts either the cut or coag contacts 144 or 142. In this regard, the angle of the toggle member 112 with respect to the handle chassis 204 in a proximal and distal respect may be maintained.

Figure 7B:
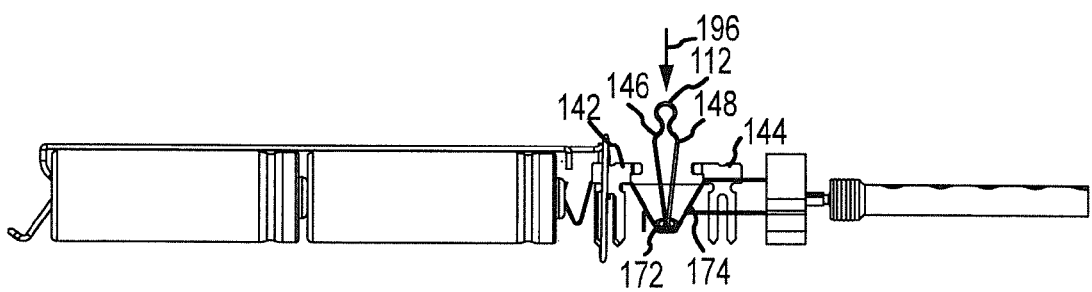

As shown in FIG. 7B, a depressive force 196 may be applied radially to the toggle member 112 with respect to the longitudinal axis 198. Accordingly, the toggle member 112 may be displaced with respect to the toggle receiver 174. In this regard, the first leg 146 and second leg 148 of the toggle member 112 may be urged towards each other. The first leg 146 and second leg 148 may be displaced to a level below where the toggle contact surface 172 is adjacent to the toggle receiver 174 such that the legs make contact with the toggle contact surface 172 disposed adjacent to the bottom of the toggle receiver 174. Correspondingly, the lighting circuit 218 may be completed as the toggle member 112 allows current to flow between the circuit member 150 and the light source connector ring 170 shown in FIG. 6. Accordingly, the position of the toggle member 112 shown in FIG. 7B represents the toggle member 112 in a position wherein only the lighting circuit is established. As can be seen, the coag contact 142 and cut contact 144 may not be contact the toggle member 112 when in this position. Furthermore, as the first leg 146 and second leg 148 of the toggle member 112 are urged together by the relative displacement of the toggle member 112 with respect to the inclined side walls of the toggle receiver 174, the distance between the toggle legs 146 and 148 and a respective contact is increased. This may help to reduce the likelihood that the electrode conductor 108 is activated in either the cut or coag operation when a user desires only the lighting circuit 218 to be active. As such, the electrode conductor 108 may not receive an electrosurgical signal and the lighting circuit 218 may be the only active circuit in the instrument when the toggle member 212 is disposed as shown in FIG. 6B.

Figure 7C:
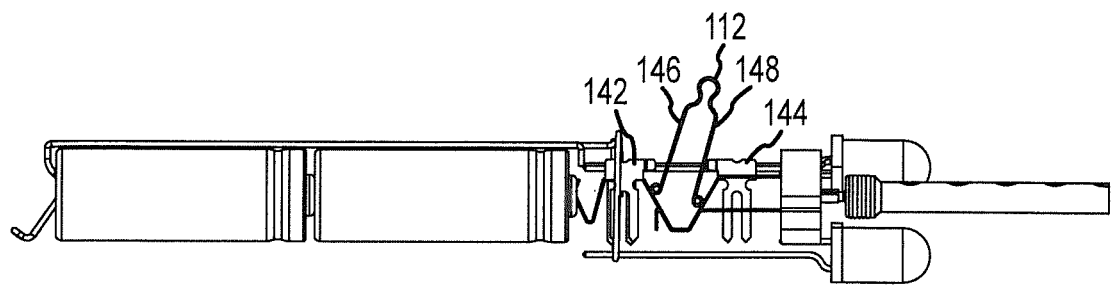

In FIG. 7C, the toggle member 112 is displaced distally such that the second leg 148 of the toggle member contacts the cut contact 144. As such, electrical communication may be established between the cut contact 144 and the second leg 148 of the toggle member 112. Because the toggle member 112 also contacts the circuit member 150, electrical communication may also be established between the first leg 146 of the toggle member 112 and the third electrosurgical path 130C. As such, the first leg 146 of the toggle member 112 establishes electrical communication between the first electrosurgical circuit 130A and the third electrosurgical circuit 130C such that the cut circuit 210 is in electrical communication with the electrode conductor 108. In this regard, once the electrode conductor 108 makes near contact with the patient, the waveform generated by the cut circuit 210 may be applied the patient to perform a cut operation.

Figure 7D:
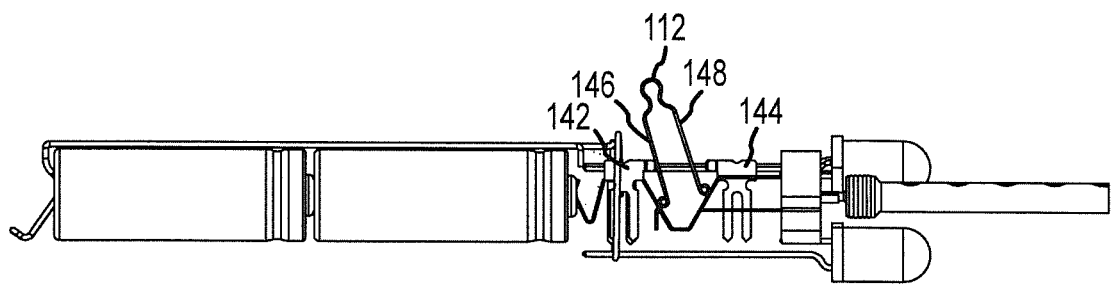

FIG. 7D illustrates a position of the toggle member 112 wherein the coag circuit 212 is in electrical communication with the electrode conductor 108. As shown, the toggle member 112 may be displaced distally such that the first leg 146 of the toggle member 112 comes into contact with the coag contact 142. As the second leg 148 of the toggle member 112 maintains contact with the toggle receiver 174, which is in electrical communication with the third electrostatic path 130C, the coag circuit 212 may be in electrical communication with the electrode conductor 108 such that if the electrode conductor 108 comes in near contact with the patient 186, the waveform generated by the coag circuit 212 may pass through the patient 186 to perform a coag operation.

Figure 7E:
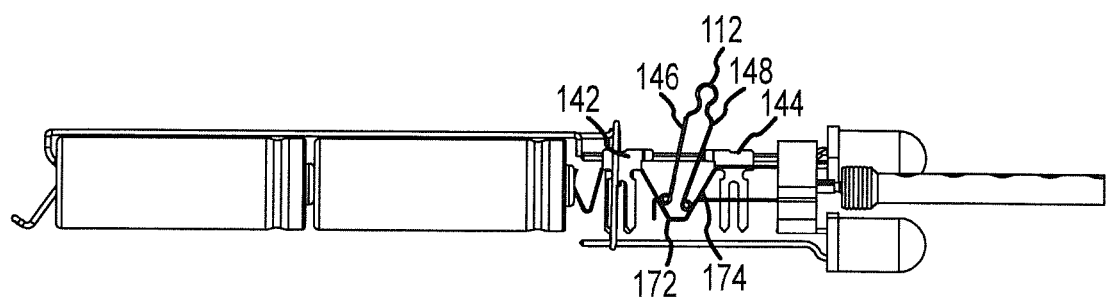

FIG. 7E depicts a position of the toggle member 112 wherein both the lighting circuit 218 is activated in addition to the cut circuit 210 being in electrical communication with the electrode conductor 108. In this regard, the toggle member 112 may be displaced such that the toggle member 112 contacts the toggle contact surface 172 to activate the lighting circuit 218 as described above with respect to FIG. 7A. In addition, the toggle member 112 and may be displaced proximally such that the second leg 148 of the toggle member 112 may also contact the cut contact 144 thus enabling a cut operation by applying the waveform generated by the cut circuit 210 to the electrode conductor 108.

Figure 7F:
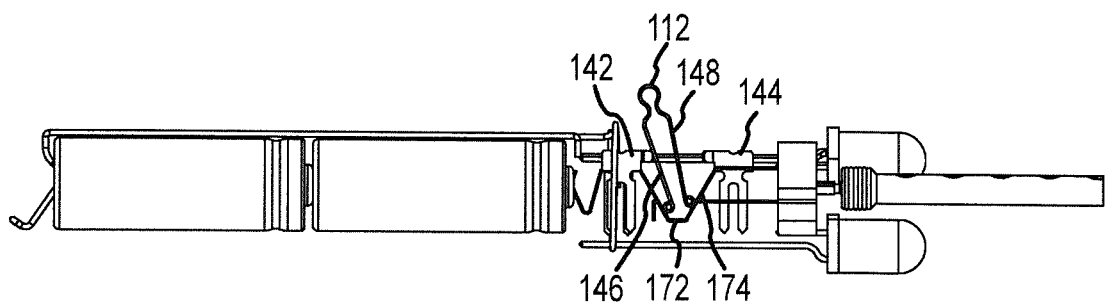

FIG. 7F depicts a position of the toggle member 112 wherein the toggle member 112 is manipulated to both activate the lighting circuit 218 as well as establish electrical communication between the coag circuit 212 and the electrode conductor 108. In this regard, the toggle member 112 may be displaced by the depressive force 196 such that the toggle member 112 contacts the toggle contact surface 172 to activate the lighting circuit 218. In addition, the toggle member 112 and may be displaced proximally such that the first leg 146 of the toggle member 112 is in contact with the coagulation contact 142. The second leg 148 of the toggle member 112 may maintain contact with the toggle receiver 174 which is in turn in electrical communication with the third electrosurgical path 130C. As such, the coag circuit 212 is in electrical communication with the electrode conductor 108 such that a waveform generated by the coag circuit 212 may pass through the patient 186 upon near contact with the electrode conductor 108.

In this regard, when in the positions shown in FIGS. 7E and 7F, the toggle member 112 may be displaceable in two dimensions. A first dimension may correspond to the proximal and distal movement of the toggle member 112 to establish contact between the coag contact 142 and the cut contact 144, respectively. In this regard, the first dimension may be parallel to the longitudinal axis 198 of the instrument 100. The toggle member 112 may be displaced in a second dimension to activate the lighting circuit 218. This second dimension may be substantially perpendicular to the longitudinal axis 198 of the instrument 100 such that the toggle member 112 is depressed within the toggle receiver 174 to activate the lighting circuit 218. As such, the second dimension may correspond to depression of the toggle member 112 with respect to the handle chassis 204.

Figure 8:
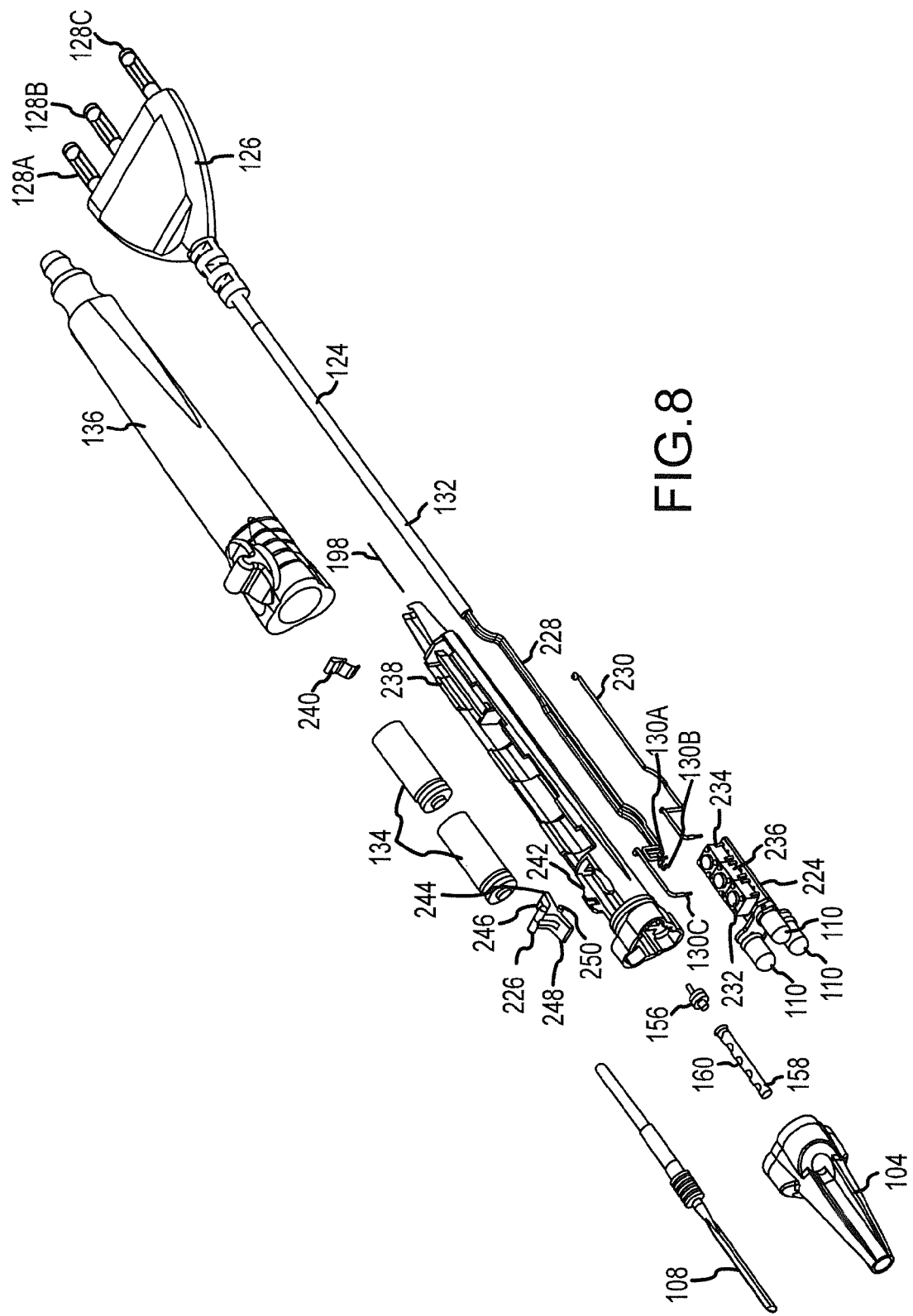
FIG. 8 is an exploded view of another embodiment of an electrosurgical instrument.

Turning to FIG. 8, another embodiment of an electrosurgical instrument 222 is depicted. The instrument 222 may include a toggle member 226 which includes a toggle beam 244 which extends proximally in a direction generally parallel with the longitudinal axis 198 of the instrument 222. The toggle beam 244 may have a proximal beam portion 246 and a distal beam portion 248. The toggle member 226 may also include a center protrusion 250 which extends downward from the toggle member 226 in a direction perpendicular to the toggle beam 244. The toggle member 226 may be supportably connected to a handle chassis 238 at a vertical slot 242. The slot 242 may accommodate a floating pivot that allows the toggle beam 244 to be displaced toward and away from a printed circuit board (PCB) 224. This floating pivot also allows the toggle beam 244 to pivot about the floating pivot point in a "see-saw" like manner. As such, the proximal beam portion 246 and distal beam portion 248 may be selectively advanced toward the PCB 224 upon the beam member 226 pivoting about this floating fulcrum.

The PCB 224 may include a plurality of contact switches similar to those described above with regard to FIG. 5. For instance, momentary contact switch modules or snap dome switches may be provided. These switches may be normally open switches which close upon contact with the toggle member 226. In one embodiment, the activation force is usually not less than about 100 g and not more than about 500 g, however, other activation forces may be used to provide different tactile feedback upon activation of the switches. These switch modules may allow for selective activation of one or more of a coag operation, a cut operation, and a lighting circuit as discussed above with respect to FIG. 5. For instance, a cut switch 232, a light switch 236, and a coag switch 234 may be arranged on the PCB 224 such that the light switch 236 is disposed between the cut switch 232 and the coag switch 234, which are respectively positioned distally and proximally from the light switch 236. The cut switch 232, lighting switch 236, and coag switch 234 may be aligned with the distal beam portion 248, center protrusion 250, and proximal beam portion 246, respectively.

In this regard, upon depression of the toggle member 226 within the vertical slot 242, the center protrusion 250 may contact the light switch 236. In turn, the light switch 236 may close. In this regard, a lighting circuit may be completed, resulting in the activation of one or more light sources. The light sources 110 may be in electrical communication with the PCB 224. A positive terminal 182 of one or more batteries 134 arranged in series or parallel may also be in electrical communication with the PCB 224. A battery lighting path 230 (e.g., comprising a wire, trace, or other conductive body) may establish electrical communication between the PCB 224 and a battery contact 240 in electrical communication with a negative terminal 180 of the one or more batteries 134. As such, upon contact of the central protrusion 250 with the light switch 236, a lighting circuit may be closed so that the light sources 110 are activated.

Additionally, a first electrosurgical path 130A, a second electrosurgical path 130B, and a third electrosurgical path 130C may be provided. These paths 130A-130C may be in respective communication with connectors 128A-128C and in turn electrosurgical signals generated by electrosurgical equipment (not shown), in a similar regard as described above. The first electrosurgical path 130A may correspond to the cut switch 232 such that when the cut switch 232 is closed, the cut signal 210 is supplied to a socket pin 156, conductive material 160, and electrode conductor 108 as described above. Accordingly, when the toggle member 226 is displaced distally with respect to the handle chassis 238, the toggle beam 244 may pivot about the floating pivot such that the distal beam portion 248 comes into contact with the cut switch 232. In this regard, distal displacement of the toggle member 226 may result in activation of a cut operation.

Similarly, the coag switch 234 may be in communication with the second electrosurgical path 130B. Upon closing of the coag switch 234, the coag signal 212 may be activated at the electrode conductor 108. In turn, the toggle member 226 may be displaced proximally such that the toggle beam 244 pivots about the floating pivot in the vertical slot 242 and the proximal beam portion 246 is advanced toward the coag switch 234. The proximal beam portion 246 may contact the coag switch 236 to activate a coag operation.

In this regard, motion of the toggle member 226 in the second dimension perpendicular to the longitudinal axis 198 of the instrument 222 results in the center protrusion 250 contacting the lighting switch 236 to activate the light sources 110. This may be performed in isolation or in conjunction with either proximal or distal advancement of the toggle member 226 in the first dimension parallel to the longitudinal axis 198 by virtue of the floating pivot. As such, the cut switch 232 and light switch 236 may be activated simultaneously by the distal beam portion 248 and center protrusion 250, respectively. Additionally, the coag switch 234 and the light switch 236 may be activated simultaneously by the proximal beam portion 246 and central protrusion 250, respectively. In this regard, the functionality associated with the five toggle member positions described above may also be realized with toggle member 226.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed is:

1. A hand-held electrosurgical instrument, comprising:
   a handle portion;
   an electrosurgical electrode supportably interconnected to and extending distally away from a distal end of the handle portion in a first direction;
   at least three light sources, for emitting light in said first direction, said at least three light sources being disposed at spaced locations about an adjoinment region adjacent to the distal end of the handle portion and activatable together to illuminate the entirety of a volume extending distally from the at least three light sources along and about a length of said electrosurgical electrode to a distal end of said electrosurgical electrode; and,
   a toggle member with a single tactile interface location supportably interconnected to the handle portion and manipulatable to effect activation of said at least three light sources together.

2. A hand-held electrosurgical instrument as recited in claim 1, further comprising:
   a nose having a proximal end interconnected to the distal end of the handle portion, wherein the nose tapers away from the distal end of the handle portion along a length of the nose towards a center axis of the electrosurgical electrode, and having a plurality of ribs having corresponding, substantially flat surfaces arranged in a triangular configuration and tapering away from the distal end of the handle portion towards a center axis of the electrosurgical electrode, wherein different ones of said at least three light sources are disposed between different adjacent ones of said plurality of ribs.

3. A hand-held electrosurgical instrument as recited in claim 1, further comprising:
   a power source supportably interconnected to the handle portion and operatively interconnected to the at least three light sources, wherein said at least three light sources are activatable by manipulation of said toggle member to emit light free from interconnection to external energy sources.

4. A hand-held electrosurgical instrument as recited in claim 1, wherein said toggle member is selectively positionable to at least a first position and a second position to effect activation of a first operational state and a second operational state of said electrosurgical instrument, respectively.

5. A hand-held electrosurgical instrument as recited in claim 4, wherein said toggle member is biased to a home position and selectively manipulatable from the home position to said first position and to said second position by a user, and wherein said electrosurgical instrument is in an inactive state when said toggle member is in the home position.

6. A hand-held electrosurgical instrument as recited in claim 5, wherein said toggle member is manipulatable to a third position to effect simultaneous activation of said first operational state of said electrosurgical instrument and said emission of light from said light emitter.

7. A hand-held electrosurgical instrument as recited in claim 6, wherein said toggle member is manipulatable to a fourth position to effect simultaneous activation of said second operational state of said electrosurgical instrument and said emission of light from said light emitter.

8. A hand-held electrosurgical instrument as recited in claim 7, wherein said toggle member is directly manipulatable between said home position and any of said first position, said second position, said third position, or said fourth position.

9. A hand-held electrosurgical instrument as recited in claim 1, wherein said handle portion includes an elastomeric handle portion that extends continuously along the handle portion and over the toggle member to seal the handle portion.

10. A hand-held electrosurgical instrument as recited in claim 1, wherein said toggle member is selectively manipulatable to a first position to effect activation of a first operational state of said electrosurgical instrument, and to a second position to effect only emission of said light.

11. A hand-held electrosurgical instrument as recited in claim 1, wherein at least a portion of said toggle member is manipulatable in a first dimension relative to said handle portion to effect activation of said at least one operational state of said electrosurgical instrument, and wherein said toggle member is manipulatable in a second dimension to effect said emission of light.

12. A hand-held electrosurgical instrument as recited in claim 1, wherein at least a portion of said toggle member is depressible relative to said handle portion to effect said emission of light.

13. A hand-held electrosurgical instrument, comprising:
   a handle portion;
   an electrosurgical electrode supportably interconnected to and extending distally away from a distal end of said handle portion in a first direction;
   at least three light sources, for emitting light in said first direction, said at least three light sources being disposed at spaced locations about an adjoinment region adjacent to the distal end of the handle portion and activatable together to illuminate the entirety of a volume extending distally from the at least three light sources along and about a length of said electrosurgical electrode to a distal end of said electrosurgical electrode; and
   a switch for activation of said at least three light sources together.

14. A hand-held electrosurgical instrument as recited in claim 13, further comprising:
   a nose having a proximal end interconnected to the distal end of the handle portion, wherein the nose tapers away from the distal end of the handle portion along a length of the nose towards a center axis of the electrosurgical electrode.

15. A hand-held electrosurgical instrument as recited in claim 14, wherein said nose further comprises:
   a plurality of ribs having corresponding, substantially flat surfaces arranged in a triangular configuration and tapering away from the distal end of the handle portion towards a center axis of the electrosurgical electrode, wherein different ones of said at least three light sources are disposed between different adjacent ones of said plurality of ribs.

16. A hand-held electrosurgical instrument as recited in claim 15, wherein said nose further comprises:
   a plurality of openings, wherein at least a portion of different ones of said at least three light sources extends through different corresponding ones of said plurality of openings.

17. A hand-held electrosurgical instrument as recited in claim 15, wherein said nose is light transmissive.

18. A hand-held electrosurgical instrument as recited in claim 15, wherein the handle portion further comprises:
   a plurality of surface projections that define a plurality of sides therebetween, wherein different ones of said at least three light sources are aligned with different ones of said plurality of surface projections.

19. A hand-held electrosurgical instrument as recited in claim 18, wherein different ones of said plurality of sides of the handle portion and corresponding different ones of said substantially flat surfaces of the nose coordinate to provide extended gripping surfaces.

20. A hand-held electrosurgical instrument as recited in claim 13, further comprising:
a power source supportably interconnected to the handle portion and operatively interconnected to each of said at least three light sources, wherein said at least three light sources are operable to emit light free from interconnection to external energy sources.

21. A hand-held electrosurgical instrument as recited in claim 20, wherein said power source comprises:
at least one battery.

22. A hand-held electrosurgical instrument as recited in claim 20, wherein said power source comprises:
at least two batteries electrically interconnected in at least one of series or parallel.

23. A hand-held electrosurgical instrument as recited in claim 13, wherein each of said at least three light sources emits at least 1,000 mcd of light.

24. A hand-held electrosurgical instrument as recited in claim 13, wherein said at least three light sources are activatable to illuminate the entirety of said volume with at least 1,000 mcd of light.

25. A hand-held electrosurgical instrument as recited in claim 13, wherein different ones of said at least three light sources emit light at corresponding different predetermined wavelengths.

26. A hand-held electrosurgical instrument as recited in claim 25, wherein said at least three light sources emit light of a color temperature of at least 3,000K.

27. A hand-held electrosurgical instrument as recited in claim 13, wherein at least a segment of said handle portion is configured to include a plurality of sides to restrict rolling of said hand-held medical instrument when disposed on a support surface.

28. A hand-held electrosurgical instrument as recited in claim 27, further comprising:
a signal cable fixedly interconnected to and extending away from the proximal end of said handle portion, said signal cable being operatively interconnected to said electrosurgical electrode for providing a signal to the electrosurgical electrode.

29. A hand-held electrosurgical instrument as recited in claim 28, further comprising:
a toggle member supportably interconnected to said handle portion and selectively manipulatable by a user to contact said switch for activation of said at least three light sources, said toggle member being located on a first side of said plurality of sides of said segment of the handle portion.

30. A hand-held electrosurgical instrument as recited in claim 28, wherein toggle member is depressible to activate said at least three light sources.

31. A hand-held electrosurgical instrument as recited in claim 27, wherein said at least two additional sides of said plurality of sides define a triangular configuration along said segment of said handle portion.

32. A hand-held electrosurgical instrument as recited in claim 27, wherein the handle portion further comprises:
a plurality of surface projections that define said plurality of sides therebetween, wherein different ones of said at least three light sources are aligned with different ones of said plurality of surface projections.

33. A hand-held electrosurgical instrument as recited in claim 32, wherein a longitudinal axis of said handle portion and a center axis of said electrosurgical electrode are one of aligned or parallel, and wherein said at least three light sources are spaced about said center axis.

34. A hand-held electrosurgical instrument as recited in claim 33, wherein said light emitter further comprises:
a triangularly-configured, light transmissive nose interconnected to said distal end of said handle portion.

35. A hand-held electrosurgical instrument as recited in claim 34, wherein said nose tapers away from said one end of said handle portion towards said center axis of said electrosurgical electrode.

36. A hand-held electrosurgical instrument as recited in claim 35, wherein said handle portion and said nose are externally configured to define a conformal transition therebetween.

* * * * *